(12) United States Patent
Majumdar (10) Patent No.: US 12,357,948 B2
(45) Date of Patent: Jul. 15, 2025

(54) HUMIDIFICATION AND SELECTIVE PERMEATION MODULE

(71) Applicant: Compact Membrane Systems, Inc., New Castle, DE (US)

(72) Inventor: Sudipto Majumdar, Newark, DE (US)

(73) Assignee: Compact Membrane Systems, Inc., New Castle, DE (US)

( * ) Notice: Subject to any disclaimer, the term of this patent is extended or adjusted under 35 U.S.C. 154(b) by 338 days.

(21) Appl. No.: 17/772,247

(22) PCT Filed: Jun. 16, 2020

(86) PCT No.: PCT/US2020/037866
§ 371 (c)(1),
(2) Date: Apr. 27, 2022

(87) PCT Pub. No.: WO2021/086447
PCT Pub. Date: May 6, 2021

(65) Prior Publication Data
US 2022/0379260 A1 Dec. 1, 2022

Related U.S. Application Data (60) Provisional application No. 62/928,956, filed on Oct. 31, 2019.

(51) Int. Cl.
*B01D 63/02* (2006.01)
*B01D 53/22* (2006.01)
(Continued)

(52) U.S. Cl.
CPC .......... *B01D 63/02* (2013.01); *B01D 53/228* (2013.01); *B01D 69/02* (2013.01); *C07C 7/144* (2013.01);
(Continued)

(58) Field of Classification Search
None
See application file for complete search history.

(56) References Cited

U.S. PATENT DOCUMENTS 4,666,468 A    5/1987   Wu
4,750,918 A    6/1988   Sirkar
(Continued)

FOREIGN PATENT DOCUMENTS

WO    WO 2019-055933 A2    3/2019

OTHER PUBLICATIONS

Huang, J et al., "Carbon Dioxide Capture Using a $CO_2$-Selective Facilitated Transport Membrane," *Ind. Eng. Chem. Res.* 2008 47 1261-1267.
(Continued)

*Primary Examiner* — Ali Z Fadhel
(74) *Attorney, Agent, or Firm* — Seed IP Law Group LLP (57) ABSTRACT

A humidification and selective permeation module in which humidification of a gaseous feed stream and selective permeation of components in the gaseous feed stream using a facilitated-transport membrane occurs within the same unit operation is disclosed. A process for separation of components in a gaseous feed stream using the humidification and permeation module combines continuous humidification of the feed stream and selective permeation using the facilitated-transport membrane.

22 Claims, 8 Drawing Sheets

(51) Int. Cl.
  *B01D 69/02*   (2006.01)
  *C07C 7/144*   (2006.01)
(52) U.S. Cl.
  CPC .......... *B01D 2053/224* (2013.01); *B01D 2325/02833* (2022.08); *B01D 2325/16* (2013.01)

(56) References Cited

U.S. PATENT DOCUMENTS

| | | | |
|---|---|---|---|
| 5,191,151 A | 3/1993 | Eriksen et al. | |
| 10,029,248 B2 | 7/2018 | Feiring et al. | |
| 2002/0100726 A1* | 8/2002 | Spearman | C10G 31/11 210/640 |
| 2009/0205490 A1* | 8/2009 | Wang | F23J 15/06 95/52 |
| 2012/0304856 A1* | 12/2012 | Kanetsuki | B01D 53/228 95/47 |
| 2014/0290479 A1 | 10/2014 | Okada et al. | |
| 2015/0025293 A1* | 1/2015 | Feiring | B01J 41/14 585/818 |
| 2019/0076786 A1* | 3/2019 | Mikawa | B01D 61/38 |
| 2022/0013797 A1* | 1/2022 | Oh | B01D 63/04 |
| 2022/0168690 A1* | 6/2022 | Tanaka | C08L 67/03 |

OTHER PUBLICATIONS

Mondal, J. et al., "Synthesis and characterization of crosslinked poly(vinyl alcohol)/poly(allylamine)/2-amino-2-hydrohydroxymethyl-1,3-prapanediol/polysulfone composite membrane for $CO_2/N_2$ separation," *Journal of Membrane Science* 2013 446 383-394.

Tong, Z. et al., "New sterically hindered polyvinylamine membranes for $CO_2$ separation and capture," *Journal of Membrane Science* 2017 543 202-211.

International Search Report for PCT/US2020/037866.
Written Opinion for PCT/US2020/037866.

\* cited by examiner

HUMIDIFICATION AND SELECTIVE PERMEATION MODULE

CROSS REFERENCE TO RELATED APPLICATIONS

This application claims the benefit of priority to U.S. Provisional Patent Application No. 62/928,956, filed on Oct. 31, 2019.

GOVERNMENT RIGHTS

This invention was made with government support under DE-SC0018876 awarded by the Department of Energy. The government has certain rights in the invention.

FIELD OF INVENTION

This invention is directed to a humidification and selective permeation module wherein humidification of a gaseous feed stream and selective permeation of components in the feed steam using a facilitated-transport membrane occurs within the same unit of operation.

BACKGROUND OF THE INVENTION

The separation of components in a gaseous feed stream through selective permeation using a facilitated-transport membrane is a promising technology for industrial separations. Example separations include alkene separation from alkanes in petrochemical refineries, carbon dioxide ($CO_2$) separation from nitrogen in flue gas, $CO_2$ separation from methane in biogas, and $CO_2$ separation from hydrogen in other industrial processes. A carrier agent for increased selective permeation may be present in the facilitated transport membrane. The carrier agent selectively and reversibly interacts with certain component(s) in the feed stream with resulting higher permeation of the interacting component(s) and higher selectivity over non interacting components. For example, membranes for selective permeation of alkenes from alkanes may incorporate a group 11 metal ion such as silver that reversibly complexes with the alkene while membranes that were useful for selective permeation of carbon dioxide from other gases may incorporate amine groups as carrier agents.

Elements for a selective permeation process usually incorporate the facilitated-transport membrane in a composite construction wherein the membrane, as a thin layer, is supported on a microporous substrate. The microporous substrate can be in the form of a hollow fiber or a flat sheet, which may also be in a spiral-wound geometry. Separations using hollow-fiber membranes are preferred for industrial applications over flat-sheet membranes as the former can provide a larger surface area per unit of module volume. Permeation module designs with hollow fibers also provide better gas or liquid distribution over the membrane surface, enhancing the overall efficiency of the facilitated-transport process. It is also well known in the art that humidification, such as through addition of water vapor to the gaseous feed stream, hydrates the facilitated-transport membrane and enhances permeance and selectivity, which can increase exponentially with increased humidification. Humidification techniques have included gas-liquid contacting where the gaseous feed stream is brought in direct contact with liquid water in a contacting tower or through mixing of the gaseous feed stream with water vapor that is formed by water vapor permeation of a microporous or nonporous barrier membrane in contact with liquid water.

Humidification of a gaseous feed stream is normally carried out in a separate unit operation ahead of a selective permeation unit operation. The humidified feed stream is subsequently directed from the humidification unit operation through conduits to the selective permeation unit operation or module containing the facilitated-transport membrane. However, water-vapor permeability is usually similar or higher than all other gases permeating the facilitated-transport membrane and it can be difficult to keep the gaseous feed stream sufficiently humidified and the facilitated-transport membrane sufficiently hydrated throughout the entire length of the permeation module. As water vapor is depleted from the gaseous feed stream, the humidity level drastically decreases in early stages of the module and is reduced throughout the remaining length. This negatively affects the overall permeability and selectivity of a facilitated-transport process requiring more membrane area for a given separation.

Sirkar in U.S. Pat. No. 4,750,918 disclosed a liquid-membrane separation process using an improved permeation module. The module contained two sets of microporous hollow fibers that separately were for gas-depletion and gas-enrichment. The hollow fibers were closely intermingled and aligned along the length of a permeation-transfer chamber within the module. The permeation-transfer chamber was filled with a selective-permeation liquid, such as an aqueous solution that may contain a soluble carrier agent and functioned as a liquid membrane. Certain components in the gaseous feed stream passed from the hollow core through the microporous walls of the gas-depletion hollow fibers into the selective-permeation liquid. The components migrated (permeated) through the selective-permeation liquid and passed through the microporous walls into the lumen of the gas-enrichment fibers. The selectivity of this separation process was high and humidification issues were minimized with this module design using a selective-permeation liquid such as an aqueous solution as the liquid membrane. However, migration of the selective-permeation liquid and condensation within the micro-pores of the relatively thick walls of the hollow fibers, notably the gas-depletion fibers, can be problematic and lead to overall reduced permeance over time as compared to a facilitated-transport membrane that is based on a nonporous film that may be much thinner.

SUMMARY OF THE INVENTION

This invention discloses a module and process for separation of a gaseous feed stream that combines concurrent humidification and selective permeation within the same unit of operation. The humidification and selective permeation module comprise two sets of hollow fibers; humidification hollow fibers containing fluid comprising liquid water within their hollow cores and facilitated-transport hollow fibers that comprise a nonporous facilitated-transport membrane. Continuous humidification of the feed stream within the module is provided by the humidification hollow fibers while selective permeation of components in the feed stream occurs through the facilitated-transport membrane of the facilitated-transport hollow fibers. The humidity level in the gaseous feed stream is advantageously maintained along the flow path of the feed stream and continuously replenished due to the humidification hollow fibers and facilitated-transport hollow fibers that may be closely overlapping, aligned, intermingled, layered, or interlaced with each other.

Furthermore, humidification within the selective-permeation module is less complex than traditional feed-gas humidification since requirements for precise temperature control of a gaseous feed stream between separate unit operations are eliminated. The humidification hollow fibers provide a more uniform hydration of the facilitated-transport membrane of the facilitated-transport hollow fibers and result in more consistent permeability and selectivity throughout the length of the module.

The humidification hollow fibers and the facilitated-transport hollow fibers are preferably porous and more preferably microporous. The hollow fibers may be constructed of the same or different materials. The humidification hollow fibers contain fluid comprising liquid water in their lumen as the source of the humidification. The walls of the humidification hollow fibers permeate water vapor but also function as a barrier preventing liquid water from entering the flow path of the gaseous feed stream and contacting the facilitated-transport membrane, which may be detrimental to overall performance. The facilitated-transport hollow fibers are also permeable and function as a porous support for a nonporous facilitated-transport membrane in a composite construction. The composite construction may include additional layers such as a high-diffusion rate (gutter) layer which can help to reduce interfacial resistance between the facilitated-transport hollow fibers and the nonporous facilitated-transport membrane and help increase overall permeance and selectivity.

The humidification and selective permeation module as described herein may be used for a wide variety of gas separations where humidification is desirable or required for better gas-separation efficiency using a facilitated-transport membrane, especially when operating at higher stage cuts where a larger fraction of the feed stream permeates the membrane. For example, the humidification and selective permeation module can be used with facilitated-transport membranes for separation of carbon dioxide from gases such as nitrogen or methane and separation of alkenes from alkanes or other gases such nitrogen. The facilitated-transport membrane may incorporate a carrier agent to increase the solubility of certain components in the gaseous feed stream through reversible reaction or complexation mechanisms and thereby preferably "facilitate" their transport through the membrane. The carrier agents may be covalently or electrostatically bound within the membrane to prevent their migration or loss from the membrane during use. Facilitated-transport membranes that are fabricated from polymer materials that are ionomers are highly useful in the invention for the above-mentioned separations. Therein, a carrier agent such as silver ions for separation of alkenes or an amine for separation of carbon dioxide may be electrostatically bound within the ionomer.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. In addition, use of "a" or "an" are employed to describe elements and components described herein. This is done merely for convenience and to give a general sense of the scope of the invention. This description should be read to include one or at least one and the singular also includes the plural unless it is obvious that it is meant otherwise.

BRIEF DESCRIPTION OF SEVERAL VIEWS OF THE DRAWINGS

Certain exemplary embodiments of the present invention are described herein. The described embodiments are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention. Certain additional terms are also used and some of them are further defined within the following detailed description of the invention.

DETAILED DESCRIPTION OF THE INVENTION

Figure 1:
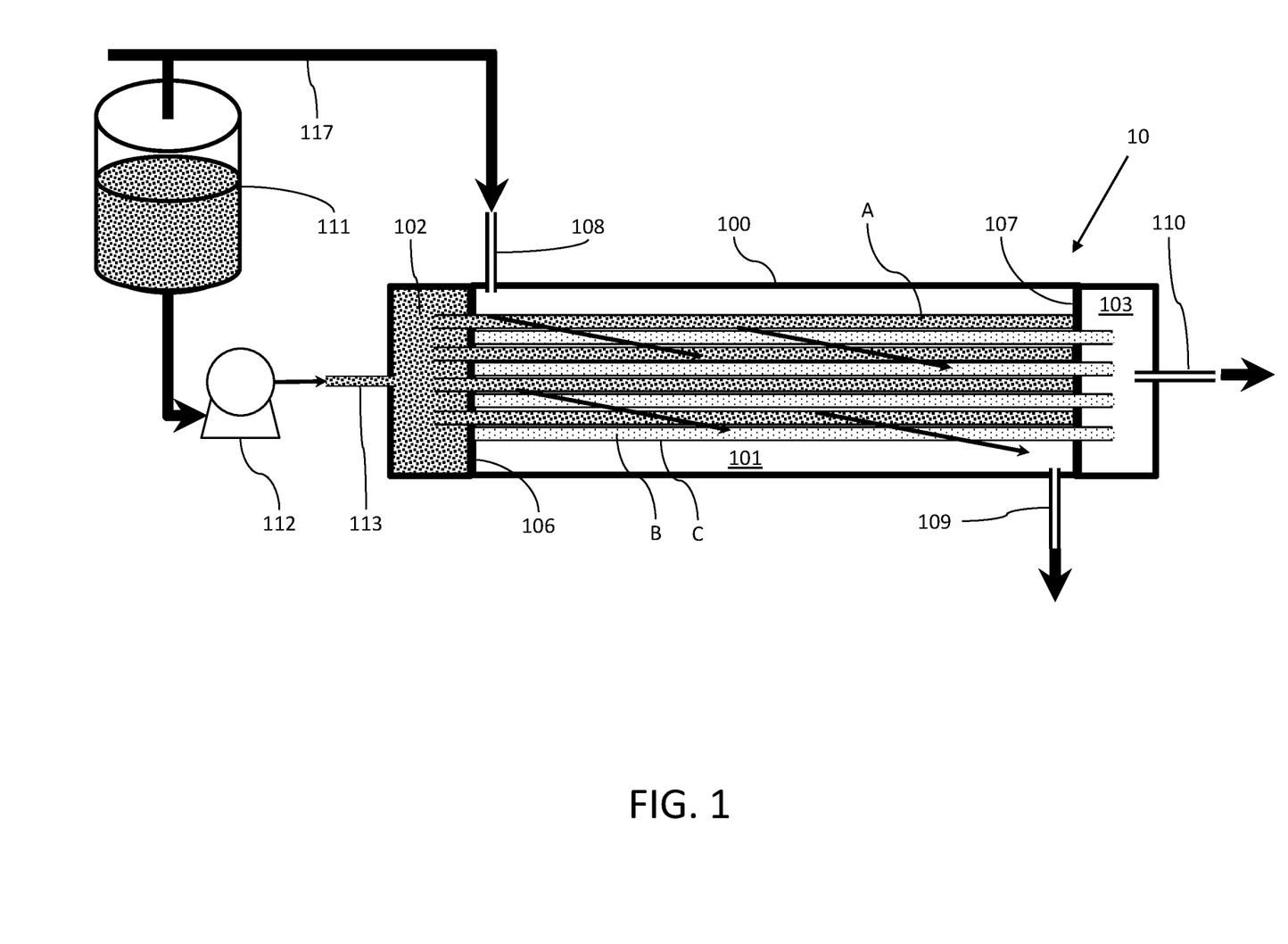
FIG. 1 shows one embodiment for a humidification and selective permeation module 10 comprising humidification hollow fibers A that are closely aligned and intermingled with facilitated-transport hollow fibers B. The humidification hollow fibers A contain fluid comprising liquid water within their hollow core, and the outside surface of facilitated-transport hollow fibers B function as a porous support for a nonporous facilitated-transport membrane C in a composite construction.
Figure 2:
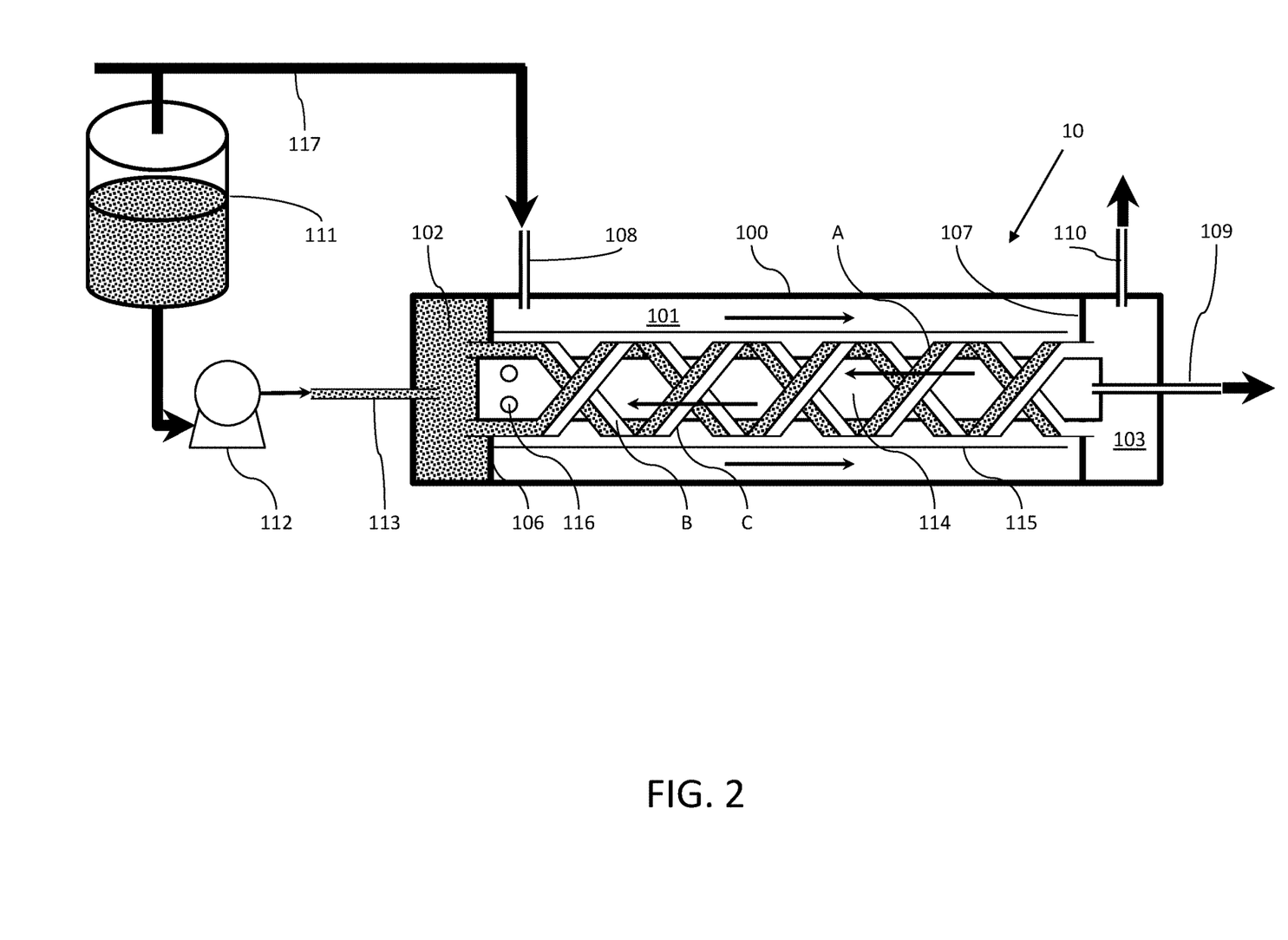
FIG. 2 shows another embodiment for a humidification and selective permeation module 10 comprising humidification hollow fibers A that are closely overlapping, and interlaced with facilitated-transport hollow fibers B. Both sets of hollow fibers are wound around a retentate core tube 114. The humidification hollow fibers A contain fluid comprising liquid water within their hollow core, and the outside surface of facilitated-transport hollow fibers B function as a porous support for a nonporous facilitated-transport membrane C in a composite construction.

A humidification and selective permeation module 10 of the invention as described herein incorporates two sets of hollow fibers; humidification hollow fibers A, which contain fluid comprising liquid water within their hollow cores, and facilitated-transport hollow fibers B that function as a porous support for a nonporous facilitated-transport membrane C in a composite construction. The hollow fibers may be arranged as separate A and B sets within the humidification and selective permeation module. Preferably, the humidification hollow fibers are in close proximity to the facilitated-transport hollow fibers. Close proximity includes humidification hollow fibers that are overlapping, aligned, intermingled, layered, or interlaced with the facilitated-transport hollow fibers. FIGS. 1 and 2 show preferred embodiments for a humidification and selective permeation module 10 incorporating the humidification and facilitated-transport hollow fibers. The module housings 100 are pressure vessels that may have a cylindrical configuration. Both figures are simplified representations that show a limited number of hollow fibers for clarity whereas a selective-permeation module for real-world industrial applications may have hundreds to thousands of fibers. The number ratio of humidification to facilitated-transport hollow fibers will be dependent on the application and their respective permeance to water vapor. The ratio is conceivably one for humidification and facilitated-transport hollow fibers having the same diameter and same permeance to water vapor. Furthermore, the number and type of hollow fibers as well as their diameter and length determine overall areas for humidification and permeation. Depending on the application, the humidification and selective permeation module length can vary substantially. Lengths from about 45-cm to about 120-cm are frequently encountered in industrial applications using hollow fiber membranes.

In FIG. 1, the humidification hollow fibers A are closely aligned with the facilitated-transport hollow fibers B along their long axes and the module housing 100. The humidification hollow fibers may be intermingled from being randomly dispersed together with the facilitated-transport hollow fibers within a bundle having a generally cylindrical cross-sectional configuration. In FIG. 2, the humidification and facilitated-transport hollow fibers are overlapping and interlaced with each other around a central retentate core tube 114. The hollow fibers are also generally aligned in the direction of the flow path for a gaseous feed stream 117. The hollow fibers in both figures are contained within a humidification-permeation transfer compartment 101 within the module housing 100. In FIGS. 1 and 2, ends of humidification hollow fibers pass through bulkhead 106 into a fluid supply chamber 102 while ends of facilitated transport hollow fibers pass through bulkhead 107 into a permeate collection chamber 103. The hollow cores of the humidification hollow fibers are open to the fluid supply chamber 102 while the hollow cores of the facilitated-transport hollow fibers are open to the permeate collection chamber 103. In FIG. 1, the opposite ends of humidification or facilitated-transport hollow fibers are closed off such as by embedding in bulkheads 107 and 106, respectively, at the time of manufacture of the bulkheads from materials such as epoxy resin. In FIG. 2, the hollow fibers are looped, and all ends of humidification or facilitated-transport hollow fibers are open and pass through bulkheads 106 or 107, respectively.

In FIGS. 1 and 2, a gaseous feed stream 117 that is under pressure enters the module housing 100 through conduit 108 into the humidification-permeation transfer compartment 101. In FIG. 2, the humidification-permeation transfer compartment 101 may additionally contain a flow directing element 115, such as a tubular sheath, which helps direct the gaseous feed stream 117 in a more parallel direction to the retentate core tube 114 and through the interlaced windings of the hollow fibers. In FIGS. 1 and 2, fluid comprising liquid water is fed from supply reservoir 111 through conduit 113 into fluid supply chamber 102. The fluid is preferably at the same or a slightly higher pressure than the gaseous feed stream and may be fed by gravity or preferably using pump 112. The fluid enters and fills the hollow cores of the humidification hollow fibers. Water vapor permeates through the walls of the humidification hollow fibers and mixes with the gaseous feed stream 117 in the humidification-permeation transfer compartment 101.

The pressure of the gaseous-feed stream provides 117 a driving force and causes certain components and water vapor within the gaseous feed stream 117 to selectively permeate the nonporous facilitated-transport membrane C, through the walls of the facilitated-transport hollow fibers B and into their hollow cores, which is at a lower pressure. In FIGS. 1 and 2, the selectively permeated and enriched components flow from the hollow cores of the facilitated-transport hollow fibers B into permeate collection chamber 103, where they exit the module housing 100 through conduit 110. In FIG. 1, the humidified-gaseous feed stream that does not permeate, which is referred to as the retentate, exits the humidification-permeation transfer compartment 101 through conduit 109. In FIG. 2, the retentate exits the humidification-permeation transfer compartment 101 through holes 116 into the retentate core tube 114, and then through conduit 109.

Both the humidification and facilitated-transport hollow fibers are preferably porous and more preferably microporous. They may be constructed of the same or different materials that may comprise polymeric materials that include but are not limited to polypropylene, polyethylene, polytetrafluoroethylene, polyacrylonitrile, polysulfone, and polyethersulfone. Porous inorganic tubes such as those comprising silica or alumina may also be suitable hollow materials in certain embodiments. The outside diameter of the hollow fibers is preferably in the range of 50 to 1000-µm, more preferably 100 to 500-µm. Smaller diameter hollow fibers have a larger surface to volume ratio and fibers that have a similar or the same size diameter can be packed more efficiently and closer together. The thickness of the hollow fiber walls is preferably in the range of 10 to 200-µm, more preferably 50 to 150-µm. The walls of the hollow fibers are preferably porous, and the mean diameter of the pores is preferably in the range of 0.002 to 0.2-µm, more preferably 0.01 to 0.05-µm. Preferred wall porosity is in the range of 0.05 to 0.9, more preferably 0.4 to 0.75.

The humidification hollow fibers contain fluid comprising liquid water within their hollow cores that is preferably static or slowly flowing as it is replenished from a supply reservoir. An exemplary fluid may consist essentially of liquid water and may be purified liquid-water being 99% or more liquid water, or liquid water that is essentially free of impurities, such as distilled liquid water. The fluid is preferably at the same or a slightly higher pressure than the gaseous feed stream. Any excess pressure should not cause the fluid to pass through the walls of the humidification hollow fibers and enter the humidification-permeation transfer compartment 101. In a preferred embodiment, the pores in the walls of the humidification hollow fibers allow water vapor to permeate but are hydrophobic. The hydrophobic nature and small size of the pores in the walls may function as a barrier, preventing the fluid from significantly penetrating and passing through the pores and contacting the nonporous facilitated-transport membrane.

In another embodiment the humidification hollow fibers may function as the porous support in a composite that includes a nonporous material that is highly permeable to water vapor but not the fluid comprising liquid water. The nonporous material may be within the pores or as a coating layer on the surface of the humidification hollow fibers. Examples of suitable nonporous materials include perfluoropolymers, such as Teflon™ AF and Nafion™ (both from The Chemours Company, Wilmington, DE). Teflon™ AF 2400 is a preferred grade that is highly permeable to water vapor and may allow the humidification hollow fibers to be operated at a higher-pressure differential. The nonporous material can be applied to the fiber as a solution using techniques such as dip-coating. The solvent is subsequently removed by evaporation to leave the nonporous material in the pores or as a coating layer, prior to assembly in the selective-permeation module. In yet another embodiment, the humidification hollow fibers may also be nonporous and constructed from a nonporous material that is highly permeable to water vapor but not the fluid comprising liquid water. Examples of such nonporous materials include the aforementioned Teflon™ AF and Nafion™ perfluoropolymers.

The facilitated-transport hollow fibers function as a porous support in a composite comprising a facilitated-transport membrane. This can include, for example, facilitated-transport membranes for separations of carbon dioxide such as disclosed in: Huang, J. et al., "Carbon Dioxide Capture Using a $CO_2$—Selective Facilitated Transport Membrane," Ind. Eng. Chem. Res. 2008 47 1261-1267; Mondal, J. et al., "Synthesis and characterization of cross-linked poly(vinyl alcohol)/poly(allylamine)/2-amino-2-hydrohydroxymethyl-1,3-prapanediol/polysulfone composite membrane for $CO_2/N_2$ separation," Journal of Membrane Science 2013 446 383-394; and Tong, Z. et al., "New sterically hindered polyvinylamine membranes for $CO_2$ separation and capture," Journal of Membrane Science 2017 543 202-211, which are all hereby incorporated by reference. A polymer material for a facilitated-transport membrane may be applied to the facilitated-transport hollow fibers as a solution using techniques such dip-coating. The solvent may be subsequently removed through evaporation to form the facilitated-transport membrane in the composite prior to assembly in the selective-permeation module. The composite may also include other layers such as a high-diffusion rate (gutter) layer which can help to reduce interfacial resistance between the facilitated transport fibers and the facilitated-transport membrane and help increase overall permeance and selectivity of the composite. For example, materials for a high-diffusion rate layer include perfluoropolymers such as Teflon™ AF (The Chemours Company, Wilmington, DE), preferably Teflon™ AF 2400. The material can be similarly applied to the facilitated transport fibers as a solution using techniques such as dip-coating prior to application of the facilitated-transport membrane.

Facilitated-transport membranes that are fabricated from polymer materials that are also ionomers are highly useful in the invention and may be used for separation of alkenes from alkanes, alkenes from non-hydrocarbon gases, in addition to separation of carbon dioxide from certain other gases. An ionomer is a copolymer that comprises both electrically neutral repeating units and repeat units having ionic groups. Ionic groups include for example sulfonic acid, sulfonate, sulfonamides, carboxylic acid, carboxylate, phosphate, phosphonium, and ammonium. Ionomers containing pendant sulfonate groups are noted for their applications in facilitated-transport membranes for separation of alkenes from alkanes such as those disclosed in Eriksen et al., "Use of silver-exchanged ionomer membranes for gas separation," U.S. Pat. No. 5,191,151; Feiring, A. E. et al., "Membrane separation of olefin and paraffin mixtures," U.S. Pat. No. 10,029,248; and Wu, M. L., "Gas separations using membranes comprising perfluorinated polymers with pendant ionomeric moieties," U.S. Pat. No. 4,666,468, which are all hereby incorporated by reference. Preferred ionomers are copolymers that are fluorinated or perfluorinated. Examples of preferred ionomers that are perfluorinated incorporate repeat units from tetrafluoroethylene and a perfluorovinylether, having a pendant sulfonate group, such as for example Aquivion® (Solvay, Houston, TX) or Nafion™ (The Chemours Company, Wilmington, DE), which are well known in the art.

The facilitated-transport membranes may contain carrier agents that are species that increase the solubility of certain components in the feed gas stream through reversible reaction or complexation mechanisms and preferably "facilitate" their transport across the membrane. The carrier agents may be covalently or electrostatically bound within the membrane to prevent their migration or loss from the membrane during use. For example, group 11 metal ions such as silver may be electrostatically bound within facilitated-transport membranes that are based on ionomers for use in separations of alkenes from alkanes. Furthermore, amines are known carrier agents for ionomers for use in carbon dioxide separations. Amine functionally may be covalently bound within a membrane or electrostatically bound within a fluorinated ionomer membrane using certain amines such as polyamines through partial reaction with an ionomer acid-group to form ammonium or alkyl-ammonium cations.

EXAMPLES

Example 1

Humidification and selective permeation module construction: A humidification and selective permeation module was constructed as outlined in FIG. 1 with the hollow fibers closely aligned and intermingled. Humidification hollow fibers were fabricated from microporous polypropylene and had a 290-μm outside diameter and a 25-μm wall thickness. Facilitated-transport hollow fibers were fabricated from microporous polyether sulfone having a 550-μm outside diameter and a 125-μm wall thickness and were configured as the porous support in a composite membrane comprising a facilitated-transport membrane for olefin-paraffin separation. The facilitated-transport membrane comprised a thin layer of a silver ionomer, as described in Feiring, A. E. et al., "Membrane separation of olefin and paraffin mixtures," U.S. Pat. No. 10,029,248, and was coated on the outside surface of the facilitated-transport hollow fibers. All hollow fibers had a length of 30-cm and eight of the humidification hollow fibers were aligned, intermingled, and initially offset by 8-cm with 3 of the facilitated-transport hollow fibers. The combined hollow fiber bundle was assembled in a 4-port module of 22-cm length and constructed from ¼" (6.3 mm) OD stainless OD tube and ¼" Swagelok® tees at each end. The module ends were sealed with epoxy resin to embed the fibers and the active length of all fibers was 19-cm. The active area of the facilitated-transport membrane on the facilitated-transport hollow fibers was 9.85-$cm^2$. The active area of humidification hollow fibers was 13.85-$cm^2$.

Example 2

Humidification and selective permeation module construction: A humidification and selective permeation module was constructed and was similar to the module outlined in FIG. 2 with the hollow fibers overlapping and interlaced.

Humidification hollow fibers were fabricated from microporous polypropylene and had a 290-μm outside dimeter and a 25-μm wall thickness. Facilitated-transport hollow fibers were fabricated from microporous polyether sulfone having a 550-μm outside diameter and a 125-μm wall thickness and were configured as the porous support in a composite membrane comprising a facilitated-transport membrane. The facilitated-transport membrane comprising a thin layer of a silver ionomer, as described in Feiring, A. E. et al., "Membrane separation of olefin and paraffin mixtures," U.S. Pat. No. 10,029,248, was coated on the outside surface of the facilitated-transport hollow fibers. The hollow fibers were wound and interlaced around a 300-mm×25-mm outer diameter retentate core tube. A flow directing element consisting of plastic wrap was added and enveloped the interlaced hollow fibers. An additional outer layer of humidification hollow fibers was added around the flow directing element, to augment humidification of dry feed gas, and complete the hollow fiber assembly. The active area of the facilitated-transport membrane on the facilitated-transport hollow fibers was 390 cm$^2$. The active area of humidification hollow fibers was 870 cm$^2$, with a top layer area of 720 cm$^2$ and interlaced area of 150 cm$^2$. The hollow fiber assembly was fitted into a 4-port cylindrical housing, that was constructed of stainless steel, to complete the humidification and selective permeation module.

Example 3

Figure 3:
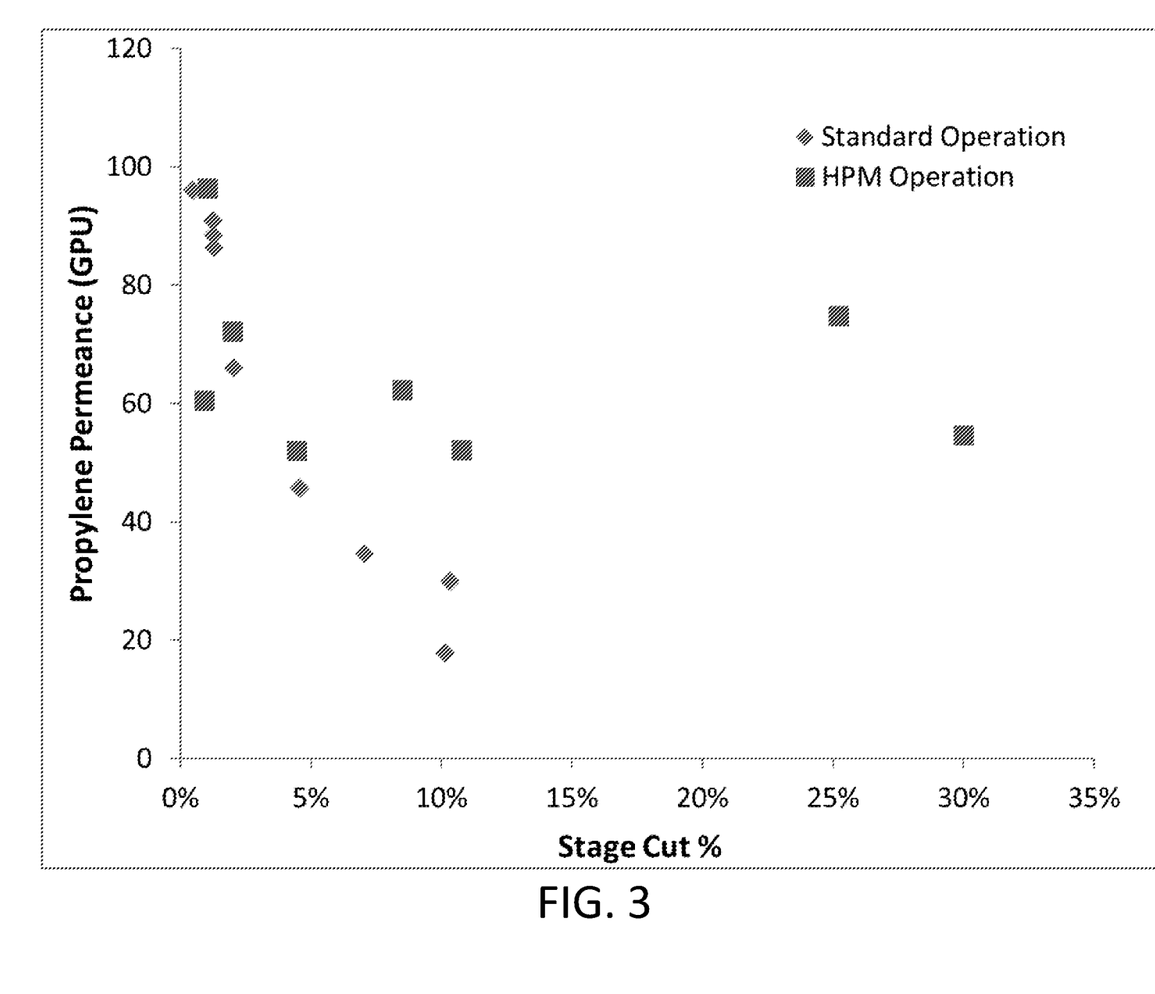
FIG. 3 shows a graph of propylene permeance versus stage cut under standard and HPM modes of operation for the humidification and selective permeation module of FIG. 1.
Figure 4:
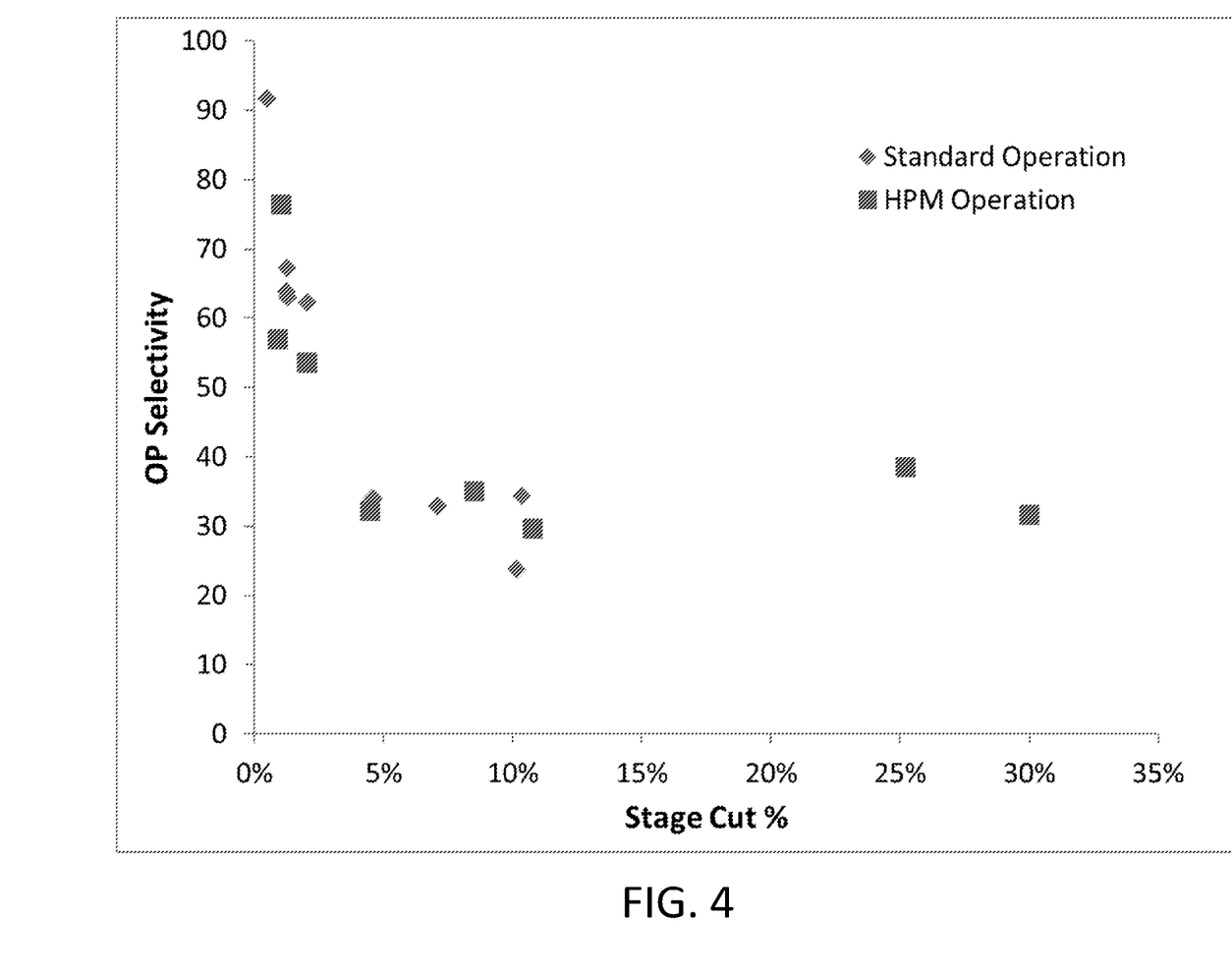
FIG. 4 shows a graph of propylene selectivity over propane (OP selectivity) versus stage cut under standard and HPM modes of operation for the humidification and selective permeation module of FIG. 1.

Separation of olefin-paraffin mixtures: The humidification and selective permeation module of Example 1 was tested for olefin-paraffin separation using feed mixtures consisting of 20% propylene and the balance propane at feed pressures up to 590 kPa. Data was collected at various stage cuts using two different modes of operation that were standard and humidification and selective permeation (HPM) mode. In the standard mode of operation, the feed gas was pre-humidified ahead of the module and without introducing water into the humidification hollow fibers. In the HPM mode of operation, water was supplied to the humidification hollow fibers to provide humidification to the initially dry feed throughout the entire length of the module. FIGS. 3 and 4 showed permeance and selectivity that was notably better for the HPM mode of operation. In the standard mode of operation, permeance and selectivity dropped drastically above a 10% stage cut. However, both the propylene permeance and OP (propylene/propane) selectivity for the HPM mode of operation were higher and more consistent at all stage cuts.

Example 4

Figure 5:
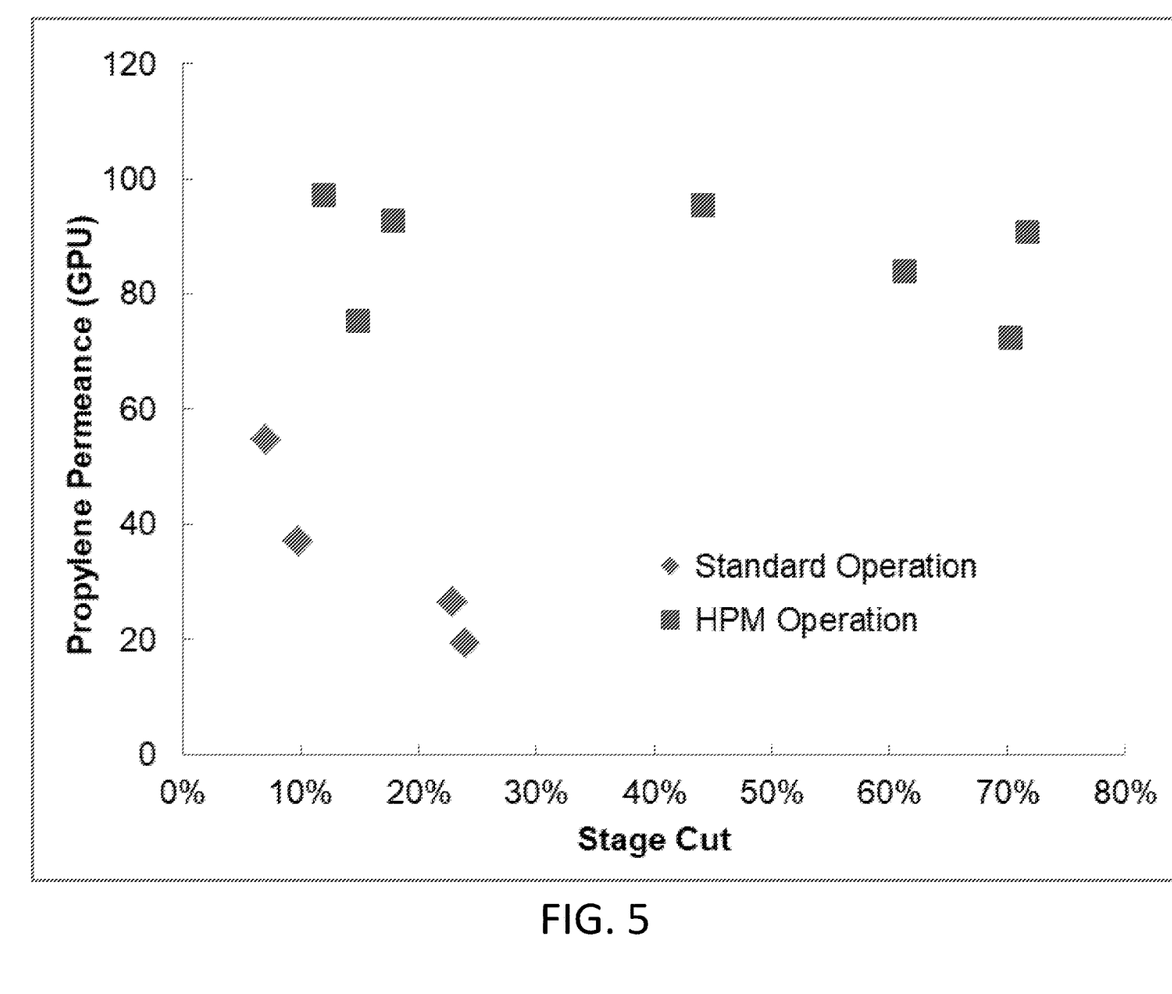
FIG. 5 shows a graph of propylene permeance versus stage cut under standard and HPM modes of operation for the humidification and selective permeation module of FIG. 2.
Figure 6:
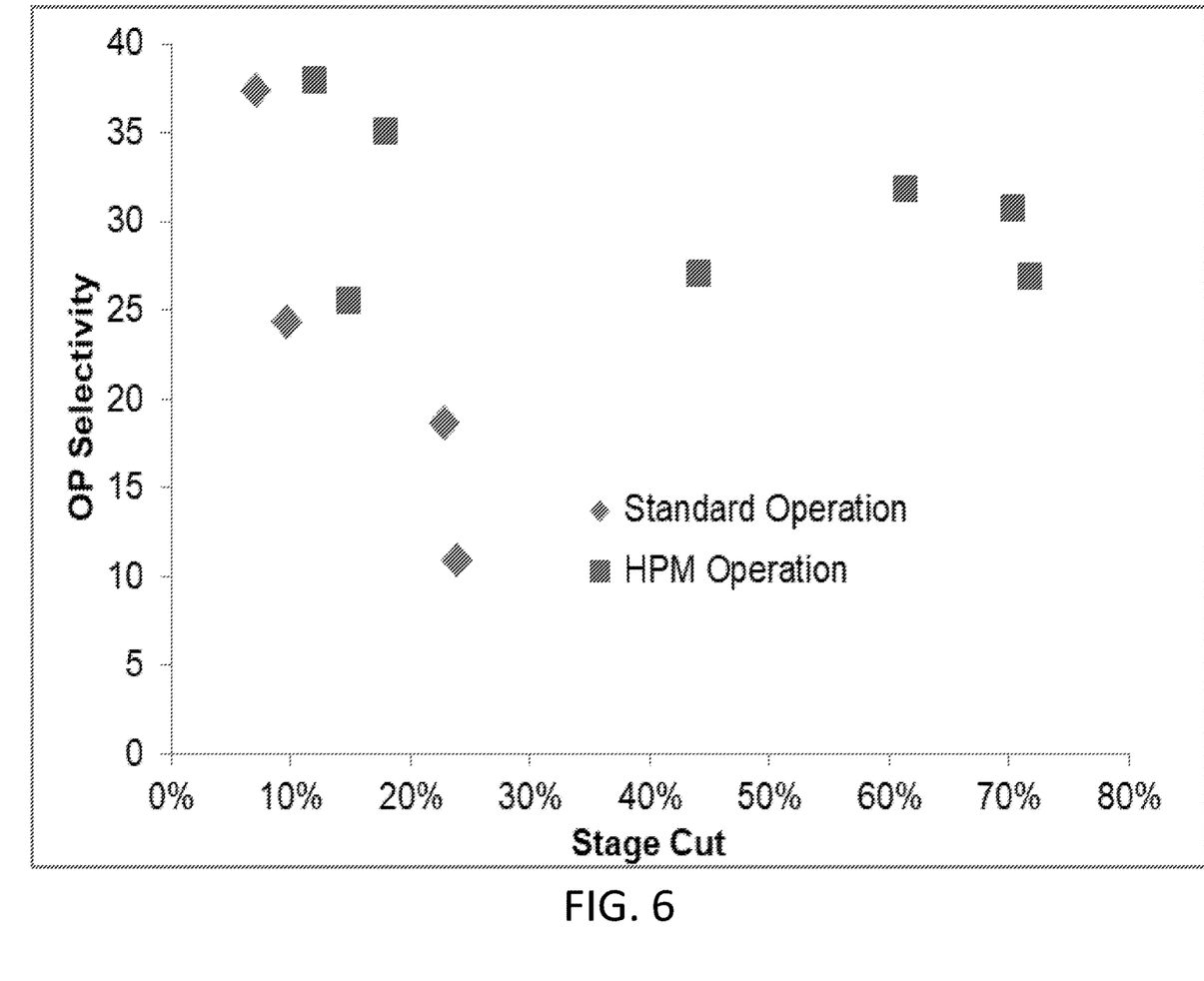
FIG. 6 shows a graph of propylene selectivity over propane (OP selectivity) versus stage cut under standard and HPM modes of operation for the humidification and selective permeation module of FIG. 2.
Figure 7:
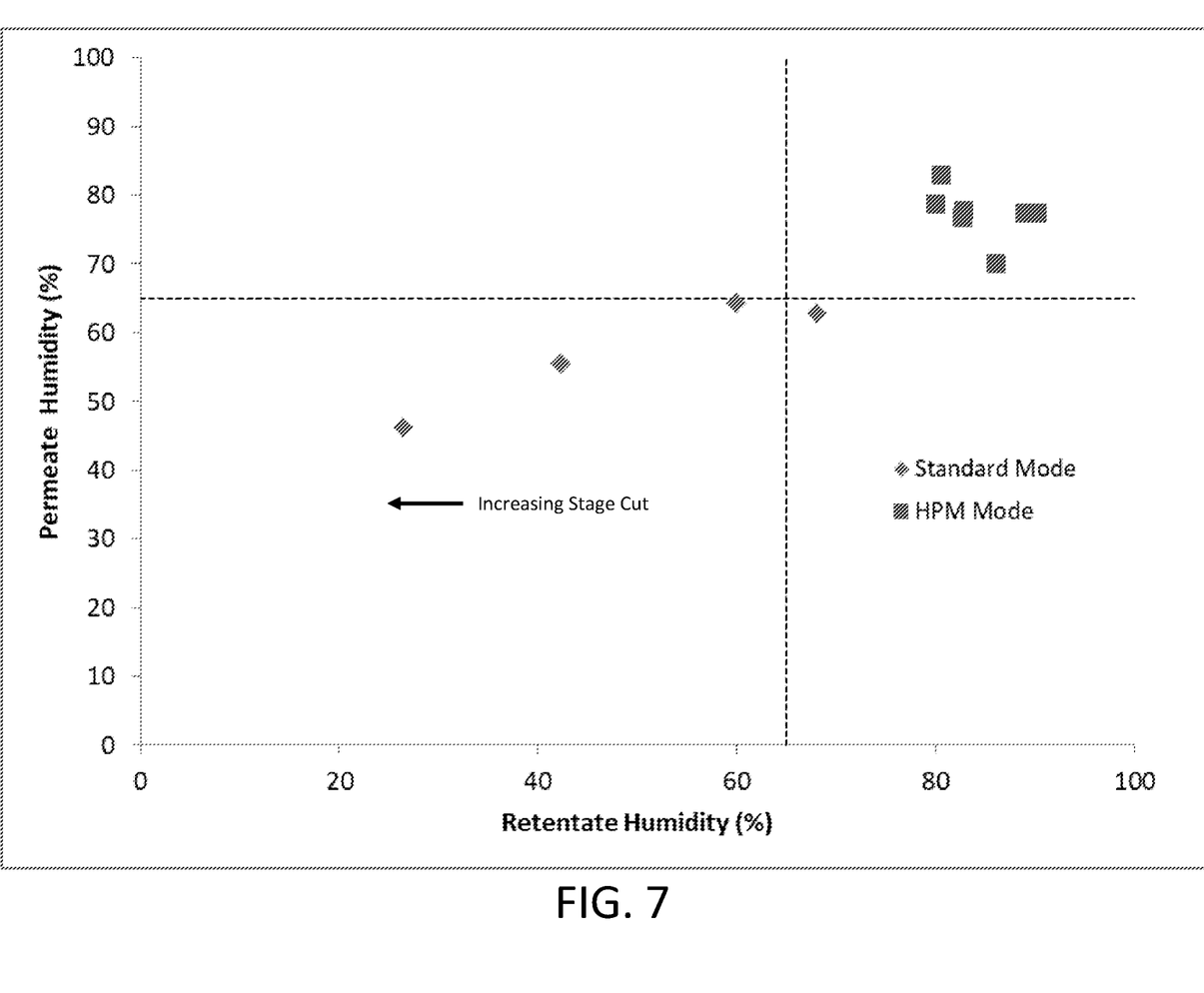
FIG. 7 shows a graph of permeate versus retentate humidity under standard and HPM modes of operation for the humidification and selective permeation module of FIG. 2.

Separation of olefin-paraffin mixtures: The humidification and selective permeation module of Example 2 was tested for olefin-paraffin separation using feed mixtures consisting of 20% propylene and the balance propane at feed pressures up to 590 kPa. Data was collected at various stage cuts using two different modes of operation that were standard and humidification and selective permeation (HPM) mode. In the standard mode of operation, the feed gas was pre-humidified ahead of the module and without introducing water into the humidification hollow fibers. In the HPM mode of operation, water was supplied to the humidification hollow fibers to provide humidification to the initially dry feed throughout the entire length of the module. FIGS. 5 and 6 showed that the HPM mode of operation was notably better than the standard mode. In the standard mode of operation, permeance and selectivity dropped drastically above a 10 to 20% stage cut. However, both the propylene permeance and OP (propylene/propane) selectivity for the HPM mode of operation were higher and more consistent at all stage cuts. Humidity level in the retentate and permeate gases in the HPM mode of operation were measured at each given stage cut and FIG. 7 showed that humidification was consistent and did not significantly change as stage cuts increased.

Example 5

Figure 8:
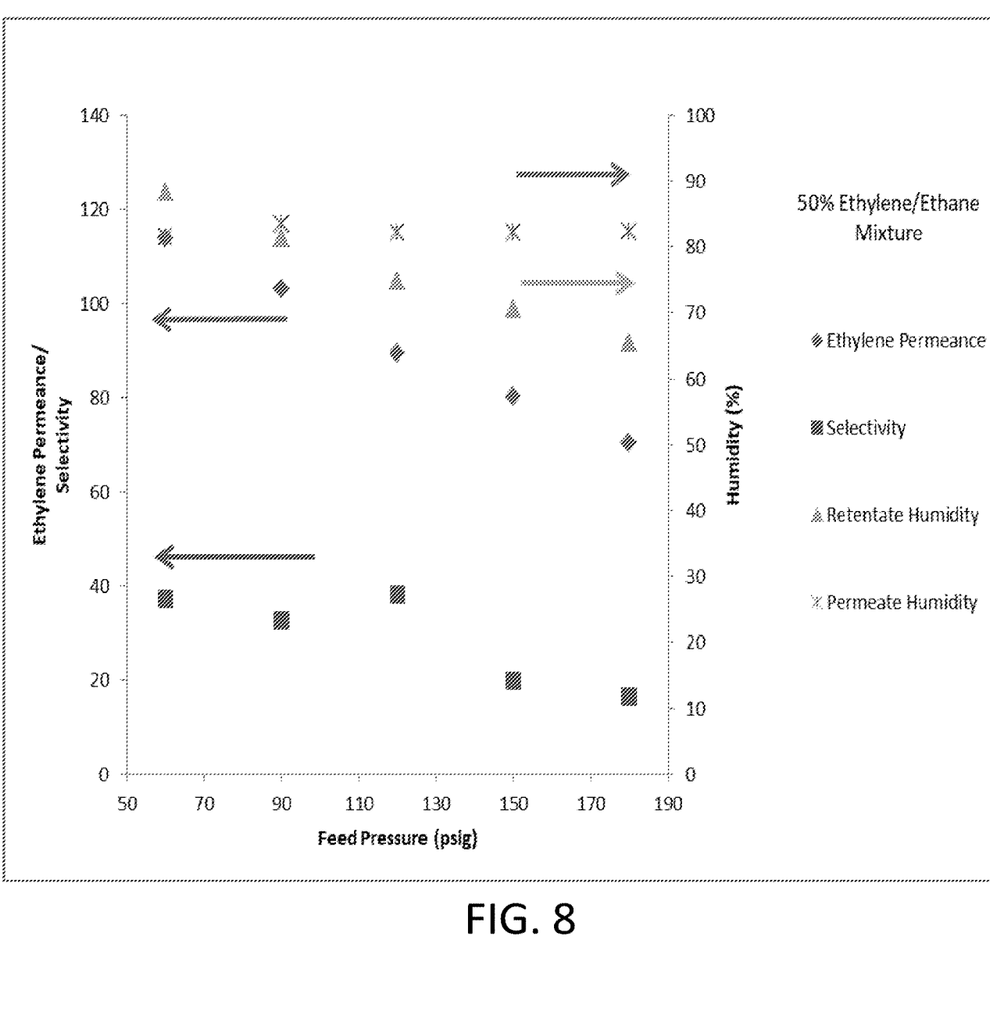
FIG. 8 shows a graph of ethylene permeance and selectivity over ethane versus feed pressure and permeate and retentate humidity level versus feed pressure under HPM mode of operation for the humidification and selective permeation module of FIG. 2.

Separation of ethylene-ethane mixtures: Separations of a 1:1 ethylene-ethane mixture were carried out with the humidification and selective permeation module as described in Example 2, at pressures between 340 and 1240 kPa under HPM mode of operation. FIG. 8 showed that gas stream humidity was maintained above 65% even at high operating pressures and resulted in good ethylene permeance and ethylene/ethane selectivity.

The invention claimed is:

1. A humidification and selective-permeation module that combines, within a single unit of operation, continuous addition of water vapor to a gaseous feed stream to form a humidified gaseous feed stream and selective permeation of components in the humidified gaseous feed steam using a facilitated-transport membrane, the humidification and selective permeation module comprising:
    a module housing configured to receive a gaseous feed stream;
    humidification hollow fibers extending within the module housing from a fluid supply chamber and not connecting to a permeate collecting chamber, each of the humidification hollow fibers having a hollow core and containing fluid comprising liquid water within the hollow core, and each of the humidification hollow fibers configured to permeate water vapor; and
    facilitated-transport hollow fibers extending within the module housing and connecting to the permeate collecting chamber but not connecting to the fluid supply chamber, each of the facilitated-transport hollow fibers comprising a nonporous facilitated-transport membrane configured to permeate water vapor and to selectively permeate at least one of the components in the gaseous feed steam.

2. The humidification and selective permeation module of claim 1, wherein the facilitated-transport membrane has a feed side and a permeate side, wherein the feed side of the facilitated-transport membrane is configured to be exposed to the humidified gaseous feed stream.

3. The humidification and selective permeation module of claim 2, wherein the humidification and selective permeation module is configured to move the feed stream through the module housing, and the facilitated-transport membrane is configured to provide a gaseous composition at the permeate side of the facilitated-transport membrane having a higher concentration of at least one of the at least two components than is present in the gaseous feed stream on the feed side of the facilitated-transport membrane.

4. The humidification and selective permeation module of claim 1, wherein one or more of the humidification hollow fibers are in close proximity to one or more of the facilitate-transport hollow fibers.

5. The humidification and selective permeation module of claim 1, wherein the humidification hollow fibers and the facilitated-transport hollow fibers each have a wall having pores, and wherein the pores have a mean pore diameter in the range of 0.01 to 0.05-μm.

6. The humidification and selective permeation module of claim 1, wherein the nonporous facilitated-transport membrane comprises an ionomer.

7. The humidification and selective permeation module of claim 6, wherein the ionomer is a perfluorinated ionomer.

8. The humidification and selective permeation module of claim 6, wherein the ionomer comprises a carrier agent selected from a group consisting of a group 11 metal ion, an amine group, and an ammonium group.

9. The humidification and selective permeation module of claim 1, wherein the humidification hollow fibers are nonporous.

10. The humidification and selective permeation module of claim 1, wherein the fluid comprising liquid water is flowing.

11. A method for separating components in a gaseous feed stream comprising:
    a) providing a humidification and selective-permeation module comprising:
        i) a module housing;
        ii) humidification hollow fibers extending within the module housing from a fluid supply chamber and not connecting to a permeate collecting chamber, each of the humidification hollow fibers having a hollow core and containing fluid comprising liquid water within the hollow core, and each of the humidification follow fibers configured to permeate water vapor; and
        iii) facilitated-transport hollow fibers extending within the module housing and connecting to the permeate collecting chamber but not connecting to the fluid supply chamber, each of the facilitated-transport follow fibers comprising a nonporous facilitated-transport membrane configured to permeate water vapor and to selectively permeate at least one of the components in the gaseous feed stream;
    c) exposing a feed side of the facilitated-transport membrane to a gaseous feed stream containing at least two components; and
    d) providing a driving force and producing a gaseous composition at a permeate side of the facilitated-transport membrane that connects to the permeate collecting chamber, wherein the gaseous composition has a higher concentration of at least one of the components than is present in the gaseous feed stream on the feed side of the facilitated-transport membrane.

12. The method of claim 11, wherein one or more of the humidification hollow fibers are in close proximity to one or more of the facilitate-transport hollow fibers.

13. The method of claim 11, wherein the humidification hollow fibers and the facilitated-transport hollow fibers each have a wall having pores, and wherein the pores have a mean pore diameter in the range of 0.01 to 0.05-μm.

14. The method of claim 11, wherein the nonporous facilitated-transport membrane comprises an ionomer.

15. The method of claim 14, wherein the ionomer is a perfluorinated ionomer.

16. The method of claim 14, wherein the ionomer comprises a carrier agent selected from a group consisting of a group 11 metal ion, an amine group, and an ammonium group.

17. The method of claim 11, wherein the humidification hollow fibers are nonporous.

18. The method of claim 11, wherein the fluid comprising liquid water is static or flowing.

19. The method of claim 11, wherein the gaseous feed stream comprises at least one component selected from a group consisting of: an alkene, alkane, carbon dioxide, and a non-hydrocarbon gas.

20. The method of claim 19, wherein:
    the gaseous feed stream comprises at least one alkene is selected from a group consisting of: ethylene, propylene, 1-butene, and 2-butene.

21. The method of claim 19, wherein the gaseous feed stream comprises at least one alkane selected from a group consisting of: methane, ethane, propane, butane, and isobutane.

22. The method of claim 19, wherein the gaseous feed stream comprises at least one non-hydrocarbon gas is selected from a group consisting of: helium, hydrogen, oxygen, and nitrogen.

* * * * *